(12) United States Patent
Greenwood et al.

(10) Patent No.: US 7,339,060 B2
(45) Date of Patent: Mar. 4, 2008

(54) PREPARATION OF CABERGOLINE

(75) Inventors: Alan Kenneth Greenwood, Hitchin (GB); Derek McHattie, Stotfold (GB); Parveen Bhatarah, Craniford (GB); Mahmoud Aloui, Hitchin (GB)

(73) Assignee: Resolution Chemicals, Ltd., Stevenage, Hertfordshire (GB)

( * ) Notice: Subject to any disclaimer, the term of this patent is extended or adjusted under 35 U.S.C. 154(b) by 0 days.

(21) Appl. No.: 11/268,118

(22) Filed: Nov. 7, 2005

(65) Prior Publication Data
US 2006/0217408 A1 Sep. 28, 2006

Related U.S. Application Data

(63) Continuation-in-part of application No. 11/100,934, filed on Apr. 7, 2005.

(30) Foreign Application Priority Data

Mar. 23, 2005 (GB) ............................ 0505965.4
Jul. 27, 2005 (GB) ............................ 0515430.7

(51) Int. Cl.
*C07D 457/04* (2006.01)
*C07D 457/02* (2006.01)

(52) U.S. Cl. .......................................... 546/69; 546/67
(58) Field of Classification Search ................. 546/69, 546/67
See application file for complete search history.

(56) References Cited

U.S. PATENT DOCUMENTS

| | | | |
|---|---|---|---|
| 3,920,664 | A | 11/1975 | Clemens et al. |
| 4,180,582 | A | 12/1979 | Kornfeld et al. |
| 4,202,979 | A | 5/1980 | Kornfeld et al. |
| 4,229,451 | A | 10/1980 | Fehr et al. |
| 4,246,265 | A | 1/1981 | Kornfeld et al. |
| 4,526,892 | A | 7/1985 | Salvati et al. |
| 4,675,404 | A | 6/1987 | Bernardi et al. |
| 4,782,152 | A | 11/1988 | Misner |
| 5,382,699 | A | 1/1995 | Honkanen et al. |
| 6,395,901 | B1 | 5/2002 | Mangia et al. |
| 2005/0085499 | A1 | 4/2005 | Bednar et al. |
| 2005/0245560 | A1 | 11/2005 | Greenwood et al. |

FOREIGN PATENT DOCUMENTS

| | | |
|---|---|---|
| CH | 535235 | 3/1973 |
| CH | 535236 | 3/1973 |
| CZ | 144634 | 7/1972 |
| CZ | 287176 | 4/1999 |
| EP | 1 591 455 | 11/2005 |
| FR | 2479829 | 10/1981 |
| GB | 1451724 | 10/1976 |
| GB | 1499420 | 2/1978 |
| GB | 2014140 A | 8/1979 |
| GB | 0409785-3 | 1/1991 |
| GB | 2103603 A | 9/2003 |
| WO | WO 01/70740 A1 | 9/2001 |
| WO | WO 01/72746 A1 | 10/2001 |
| WO | WO 01/72747 | 10/2001 |
| WO | WO 03/078392 A2 | 9/2003 |
| WO | WO 03/078433 A2 | 9/2003 |
| WO | WO 2004/094368 | 11/2004 |
| WO | WO 2004/101510 A2 | 11/2004 |

OTHER PUBLICATIONS

Candiani et al., The Ligand Effect in Copper (I)—Catalyzed Chermoselective Amide, 605-606 (1995).
Sabatino et al., X-Ray Crystal Structure and Conformational Analysis of Cabergoline . . . , Il Farmaco, 50(3): 175-178 (1995).
Brambilla et al., Synthesis and Nidation Inhibitory Activity . . . , New Eur. J. Med. Chem., 24: 421-426 (1989).
Montegani et al., Synthesis of Tritium and Carbon-14 Labeled N . . . , J. Labelled Compd. Radiopharm. 29(5): 519-533 (1991).
Ohno et al., Synthesis and Structure . . . , Chem. Pharm. Bull., 42(7): 1463-1473 (1994).
Battaglia et al., Dispostion . . . , Xenobiotica 23(12): 1377-1389 (1993).
Benes et al., Epimerization of Esters of Stereoisomeric . . . , Coll. Czech. chem. Commun. 48: 1333-1340 (1983).
Stoll et al., Die Dihydroderivate der Rechtscdrehenden . . . , Helv. Chim. Acta 29(3): 635-653 (1946).
Stadler, Eine Einfache Veresterungsmethode im Eintopf-Verfahren, Helv. Chim. Acta 61(5): 1675-1681 (1978).
Fehr et al., Demthylierung des Lysergsauregerustes, Helv. Chim. Acta 53(8): 2197-2201 (1970).
Krepelka et al., Some 6-Alkyl Derivatives of D-8-Cyanomethyl . . . , Coll. Czech. Chem. Commun. 42: 1209-1215 (1977).
Jacobs et al., Isomeric Dihydrolysergic Acids and the Structure of Lysergic Acid, J. Biol. Chem. 227-239 (1936).
Cerney et al., Mutterkornalkaloide, Pharmazie 26(12) 740-741 (1971).
Kornfield et al., The Total Synthesis of Lysergic Acid, J. Am. Chem. Soc. 3087-3114 (1956).
Zhang et al., Zhongguo Yi Xue Ke Xue Yuan Xue Bao, 6(1): 70-72 (1984).
Kleeman et al., Pharmaceutical Substances, 4th Ed., 312-313.

(Continued)

*Primary Examiner*—Charanjit S. Aulakh
(74) *Attorney, Agent, or Firm*—Rakoczy Molino Mazzochi Siwik LLP

(57) ABSTRACT

A method of preparing cabergoline Form I, comprising forming a solvate including cabergoline and a p-disubstituted benzene of formula (A) or 1,3,5-trimethylbenzene and obtaining cabergoline Form I from the solvate. Another aspect of the present invention provides a method for preparing cabergoline Form I comprising dissolving cabergoline in p-disubstituted benzene or 1,3,5-trimethylbenzene and recovering the cabergoline Form I polymorph, suitably by direct crystallization of Form I or by recovery of a solvate which can be converted to Form I. Another aspect of the present invention provides a novel cabergoline polymorph designated cabergoline Form $F_B$ and a method of preparing said polymorph by dissolving or forming a solvate of cabergoline in fluorobenzene and recovering cabergoline Form $F_B$.

95 Claims, 14 Drawing Sheets

OTHER PUBLICATIONS

Dollery et al., Therapeutic Drugs, 2nd Ed., C1-C4 (1999).
Parfitt, The Pharmaceutical Press, Martindale, 32nd Ed. 1135-1136 (1999).
Gottwald et al., Ann. Pharmacother. 31: 1205-1217 (1997).
Wiseman et al., Cabergoline—A Review of its Efficacy in the Treatment of Parkinson's Disease, CNS Drugs 12 (6): 485-497 (1999).
Ichikawa et al., Nippon Yakurigaku Zasshi 117: 395-400 (2001).
The Merck Index, 13th Ed., 270 (2001).
Gotor, Non-Conventional Hydrolase Chemistry: Amide and Carbamate Bond Formation Catalyzed by Lipases, Bioorg. Med. Chem. 7: 2189-2197 (1999).
Crider et al., Convenient Synthesis of 6-Nor-9,10-Dihydrolysergic Acid Methyl Ester, J. Pharm Sci. 70 (12): 1319-1321 (1981).
Olofson et al., A New Reagent for the Selective, High Yield N-Dealkylation of Tertiary Amines . . . , J. Org. Chem. 49: 2081-2082 (1984).
Olofson et al., Tests of a Piperidino Mask for the Protection of Functionalized Carbon Sites in Multistep Syntheses, J. Org. Chem. 49: 2795-2799 (1984).
Allievi et al., Quantitative Determination of Cabergoline in Human Plasma . . . , Rapid Commun. Mass Spectrom. 12: 33-39 (1998).
Prelog et al., Helv. Chim. Acta 39: 498-504 (1956).
Vaughan, Acylalkylcarbonates as Acylating Agents for the Synthesis of Peptides, J. Am. Chem. Soc., 73: 3547 (1951).
Walker, The Functional Gropu Selectivity of Complex Hydride Reducing Agents, Chem. Soc. Rev. 5: 23-51 (1976).
Kornet et al., The Borane Reduction of Amido Esters, J. Org. Chem. 33(9): 3637-3639 (1968).
Lalancette et al., Reductions of Functional Groups with Sulfurated Borohydrides, Synthesis 526-532 (1972).
Cainelli et al. Farmaco, Ed. Sci. 22(6): 456-462 (1967).
Larock, Comprehensive Organic Transformations, 2nd Ed., Wiley VCH 1940-1977 (1999).

Humphrey et al., Chemical Synthesis of Natural Product Peptides: Coupling Methods for the Incorporation of Noncoded Amino Acids into Peptides, Chem. Rev. 97: 2243-2266 (1997).
Carpino et al., Racemization Studies During Solid-Phase Peptide Synthesis Using Azabenzotriazole-Based Coupling Reagents, Tetrahedron Lett. 35(15): 2279-2282 (1994).
Spetzler et al., Novel Acylation Catalysts in Peptide Synthesis . . . , J. Chem. Soc., Perkin Trans. 1: 1727-1731 (1998).
Gibson et al., Bis[[4-(2,2-dimethyl-1,3-dioxolyl)]methyl]-carbodiimide (BDDC) . . . , J. Org. Chem. 59: 7503-7507 (1994).
Gibson et al., Carboxy Terminus Coupling 1,1'-Carbonylbis(3-methylimidazolium triflate) (CBMIT) in the Presence of Cu(II) Salts, J. Org. Chem. 60: 2615-2617 (1995).
Soledad De Castro et al., Lipase-Catalyzed Synthesis of Chiral Amides . . . , Tetrahedron 54 2877-2892 (1998).
Sanchez et al., Candida Antarctica Lipase-Catalyzed Double Enantioselective Aminolysis Reactions, J. Org. Chem. 64: 1464-1470 (1999).
Stepanov, Proteinases as Catalysts in Peptide Synthesis, Pure and Applied Chem. 68(6) 1335-1339 (1996).
Marzoni et al., 6-Methylergoline-8-Carboxylic Acid Esters as Serotonin Antagonists, J. Med. Chem. 30: 1823-1826.
Co-Pending U.S. Appl. No. 11/100,934, entitled "Preparation of Cabergoline," Bhatarah et al.
Co-Pending U.S. Appl. No. (To be assigned), entitled "Production of Cabergoline and Novel Polymorphic Form Thereof," Greenwood et al.
Caira, M.R., "Crystalline Polymorphism of Organic Compounds," Topics in Current Chemistry 198:164-207 (1998).
Search report for corresponding Great Britain Appl. No. GB 0515430.7, dated Nov. 16, 2005.
International Search Report for corresponding International Application No. PCT/GB2006/002784, dated Jan. 12, 2006.

PREPARATION OF CABERGOLINE

This application is a continuation-in-part of U.S. patent application Ser. No. 11/100,934 filed on Apr. 7, 2005, which claims priority to United Kingdom patent application no. GB 0505965.4, filed on Mar. 23, 2005. This application additionally claims priority to United Kingdom patent application no. GB 0515430.7, which was filed on Jul. 27, 2005. The above-named UK applications are hereby incorporated by reference in their entirety.

FIELD OF THE INVENTION

The present application relates to the preparation of cabergoline, in particular to a new process for preparing cabergoline Form I and to the production of a novel cabergoline polymorph Form $F_B$.

BACKGROUND OF THE INVENTION

Cabergoline is an ergoline derivative with formula 1-((6-allylergolin-8β-yl)-carbonyl)-1-(3-dimethylaminopr It is known for treatment of a number of diseases, including CNS disorders, reversible obstructive airways disease, prolactin inhibition, for controlling intra-ocular pressure and for treating glaucoma.

A number of different forms of cabergoline are known and, by way of example, PCT patent publication no. WO 01/72747 describes cabergoline Form II and PCT patent publication no. WO 01/72746 describes cabergoline Form VII.

Preparation of cabergoline Form I is described in PCT patent publication nos. WO 01/70740, WO 03/078392 and WO 03/078433. For example, PCT patent publication no. WO 01/70740 teaches the preparation of crystalline cabergoline Form I from a solvent comprising a toluene/diethyl-ether mixture whereas PCT patent publication nos. WO 03/078392 and WO 03/078433 teach crystalline cabergoline Form I that is obtained by drying a solvate of cabergoline and toluene.

Pending U.K. patent application no. GB 0409785.3 teaches a process for preparing cabergoline Form I of high yield and purity and with desirable particle size distribution using ethylbenzene optionally in conjunction with an anti-solvent such as n-heptane. GB 0409785.3 further describes a cabergoline ethylbenzene solvate.

A series of cabergoline polymorphs are also described in PCT patent publication no. WO 2004/101510.

It is desired in the present invention to prepare crystalline cabergoline Form I having high purity. It is also desired to prepare cabergoline having a particle size (following crystallization) which is relatively small and which requires no or relatively little milling to obtain the particle size desired in the eventual pharmaceutical product. Milling and other such processing is undesirable as it tends to lead to conversion of pure polymorphic forms of cabergoline into polymorphic mixtures. One problem with the methods described in PCT patent publication no. WO 03/078433, for example, is that crystals of cabergoline Form I obtained have a relatively large particle size.

It is also desired to provide a process for preparation of cabergoline in which conversion of an intermediate solvate to the final cabergoline Form I product is quick and efficient. A difficulty with known processes for this conversion is that protracted drying periods are required to remove the solvent from the solvate-in excess of 48 hours-for the methods set forth in PCT patent publication no. WO 03/078433.

SUMMARY OF THE INVENTION

One aspect of the present invention provides a method for preparing cabergoline Form I comprising dissolving cabergoline in a p-disubstituted benzene of formula (A)

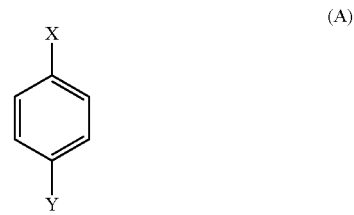

(A)

where X is a halogen, and Y is selected from the group consisting of a halogen or a lower alkyl, and recovering the cabergoline Form I polymorph from the solution in the p-disubstituted benzene, suitably by direct crystallization or recovery of a solvate which can be converted into cabergoline Form I. Another aspect of the present invention provides a new polymorphic form of cabergoline, designated herein as cabergoline Form $F_B$, which may be obtained by a process comprising forming a solvate of cabergoline and fluorobenzene and recovering cabergoline Form $F_B$ from that solvate.

DETAILED DESCRIPTION OF THE INVENTION

Figure 1:
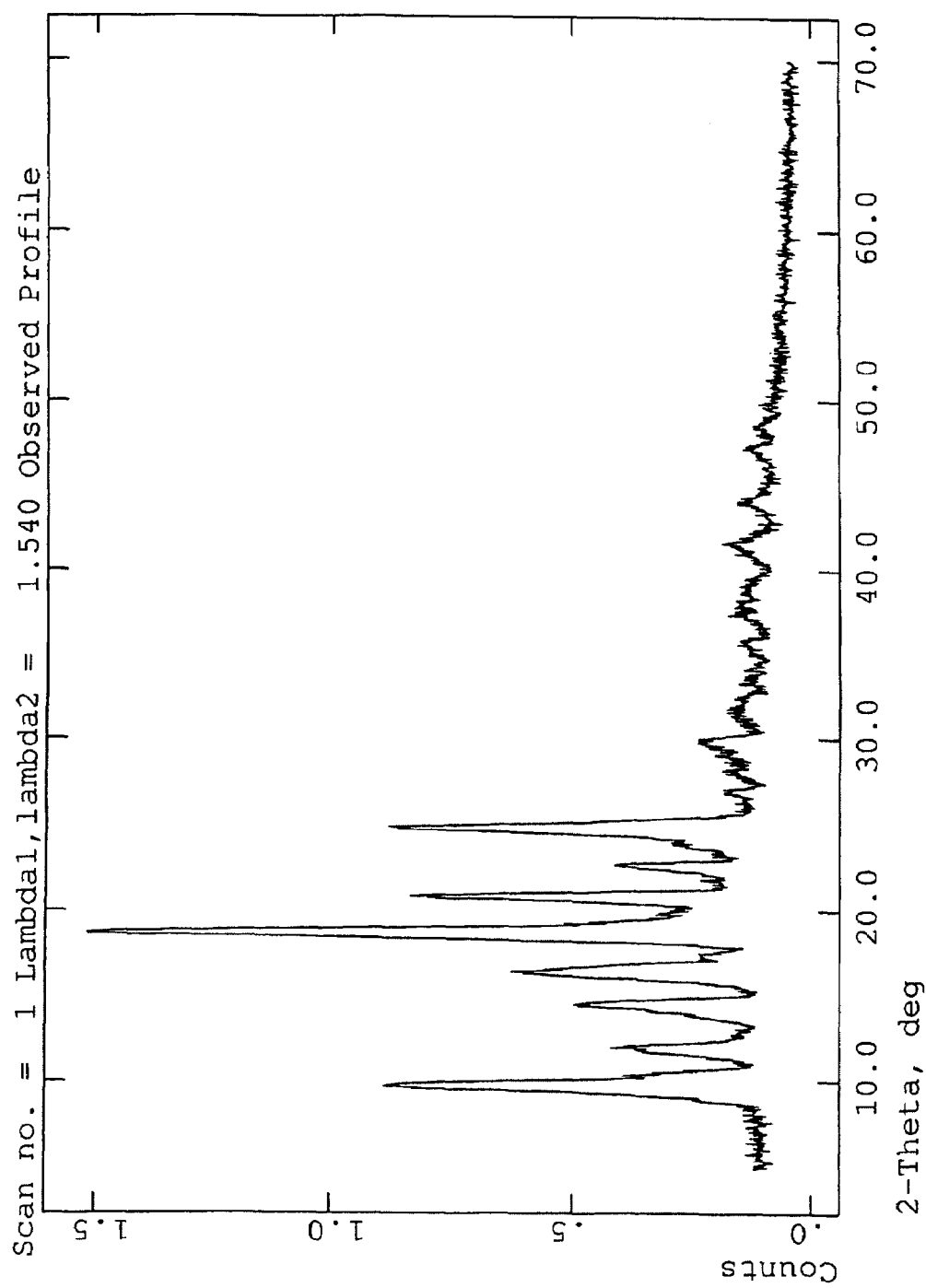
FIG. 1 is an X-ray powder diffraction pattern for the cabergoline Form I obtained using 4-fluorotoluene as solvent (Example 1)
Figure 2:
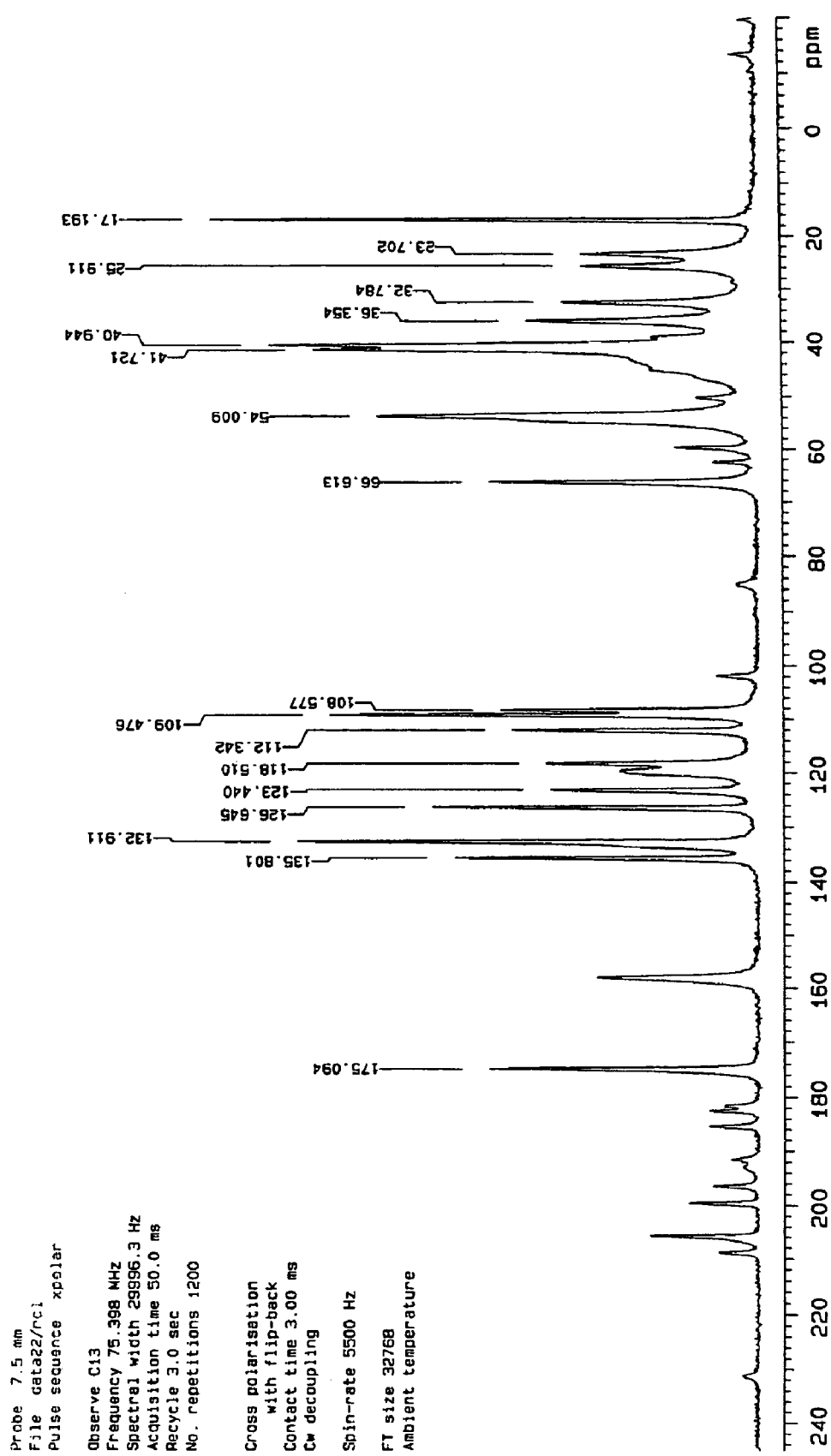
FIG. 2 is a $^{13}C$ CPMAS spectrum of cabergoline Form I obtained using 4-fluorotoluene as solvent (Example 1).
Figure 3:
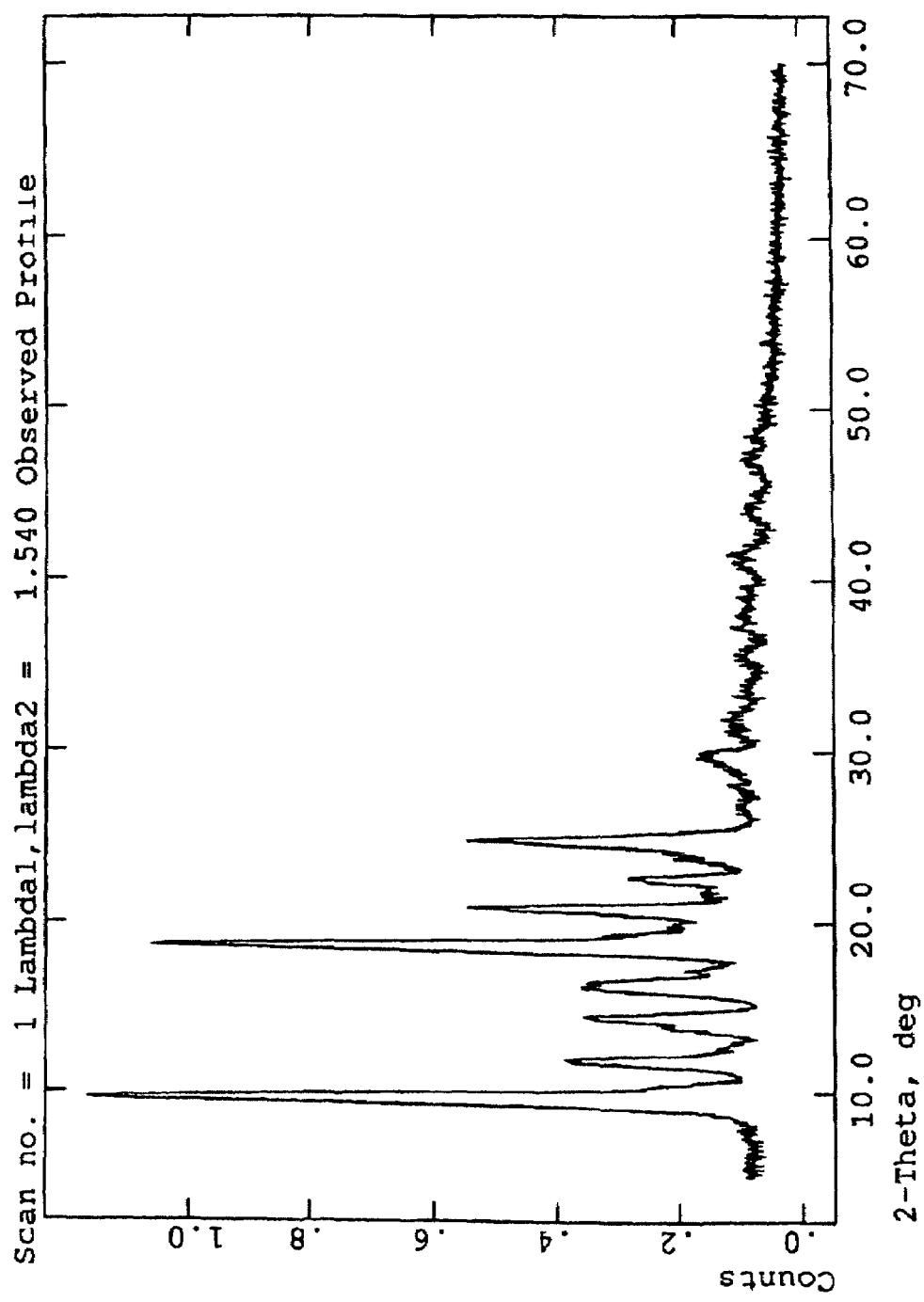
FIG. 3 is an X-ray powder diffraction pattern of cabergoline Form I obtained using 1-chloro-4-fluorotoluene as solvent (Example 4)
Figure 4:
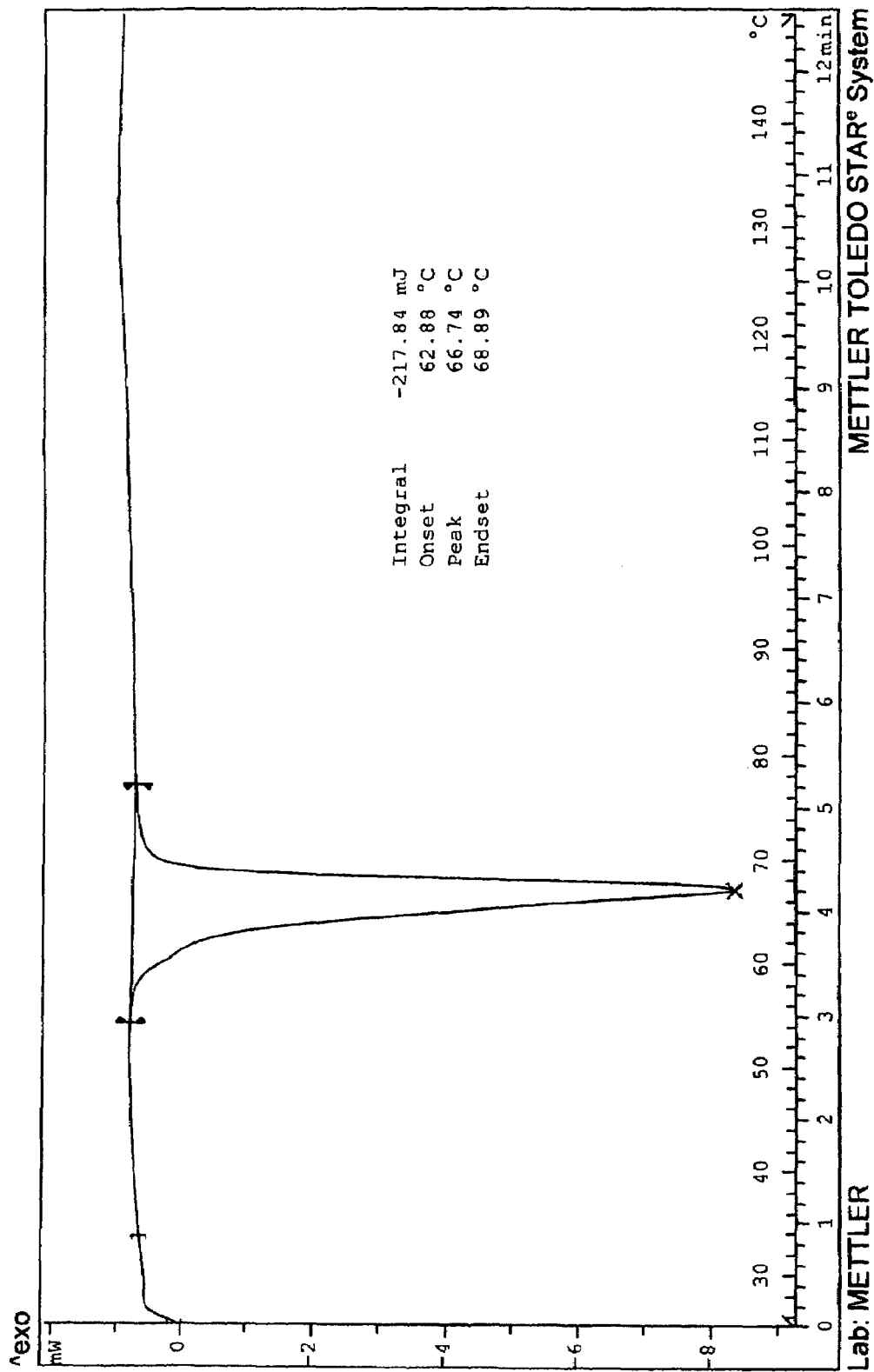
FIG. 4 is a differential scanning calorimetry (DSC) trace of damp cabergoline Form I obtained using 1-chloro-4-fluorobenzene as solvent (Example 4).
Figure 5:
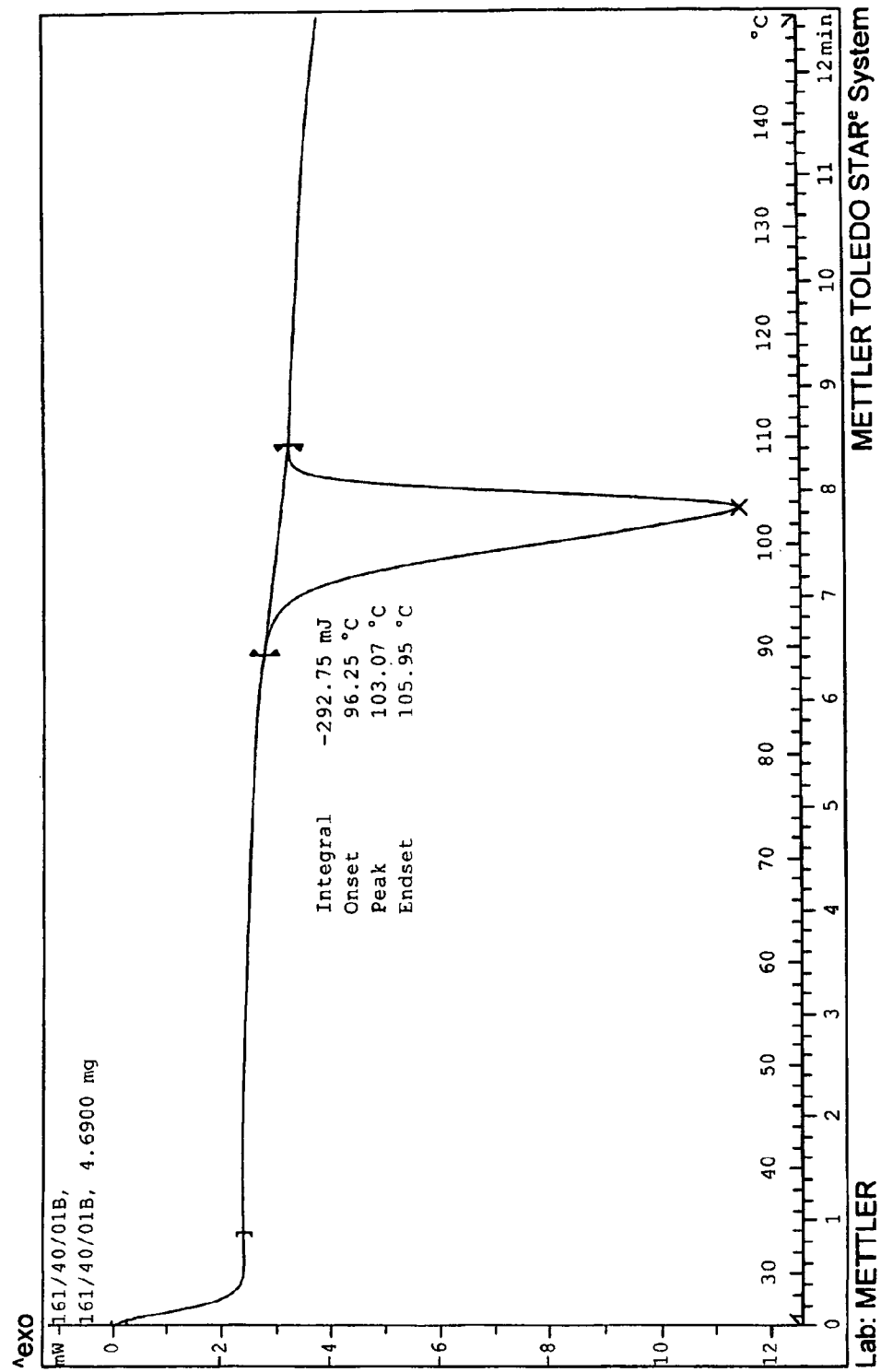
FIG. 5 is a differential scanning calorimetry (DSC) trace of dry cabergoline Form I obtained using 1-chloro-4-fluorobenzene as solvent (Example 4).
Figure 6:
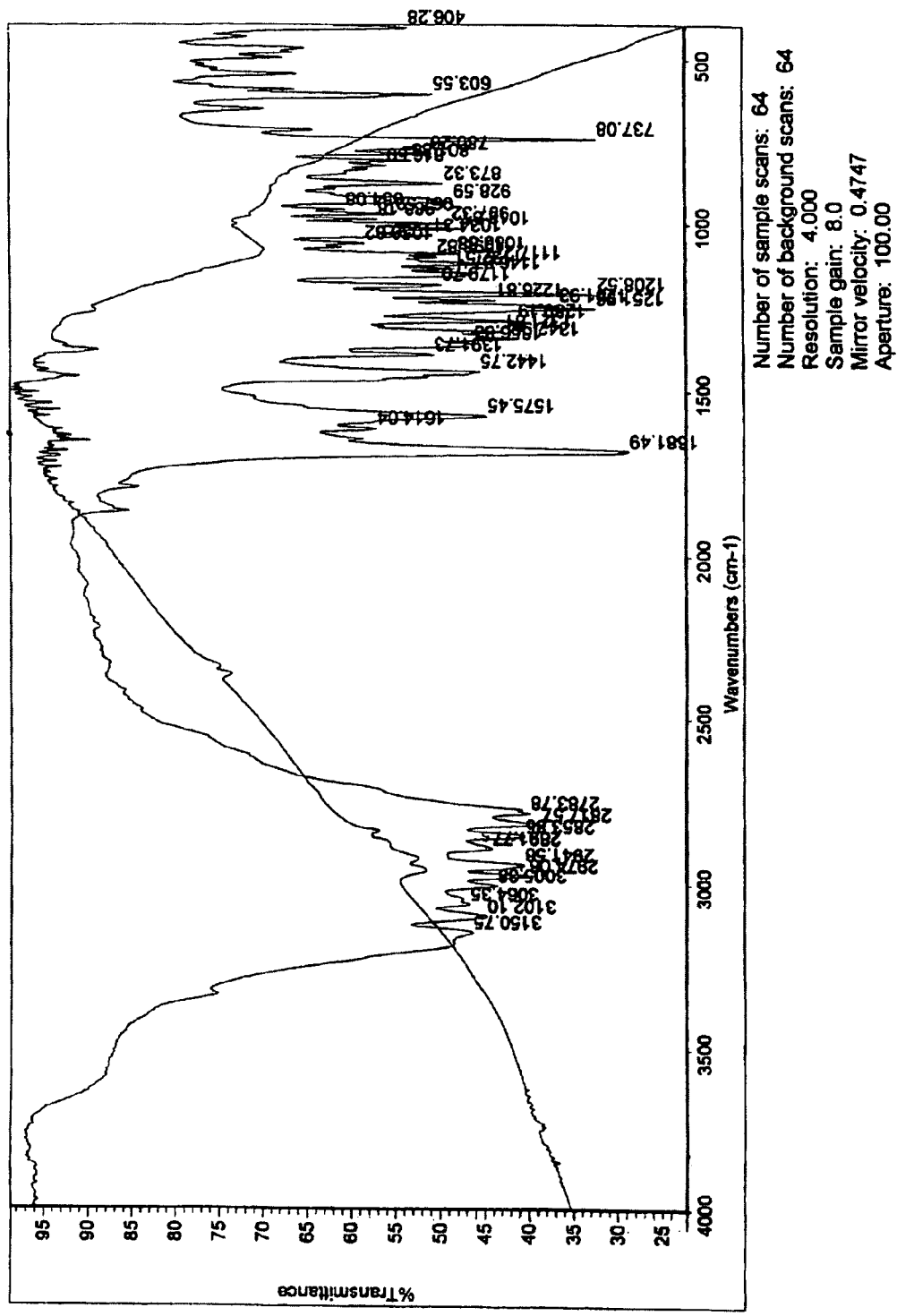
FIG. 6 is an FTIR scan of cabergoline Form I obtained using 1-chloro-4-fluorobenzene as solvent (Example 4).
Figure 7:
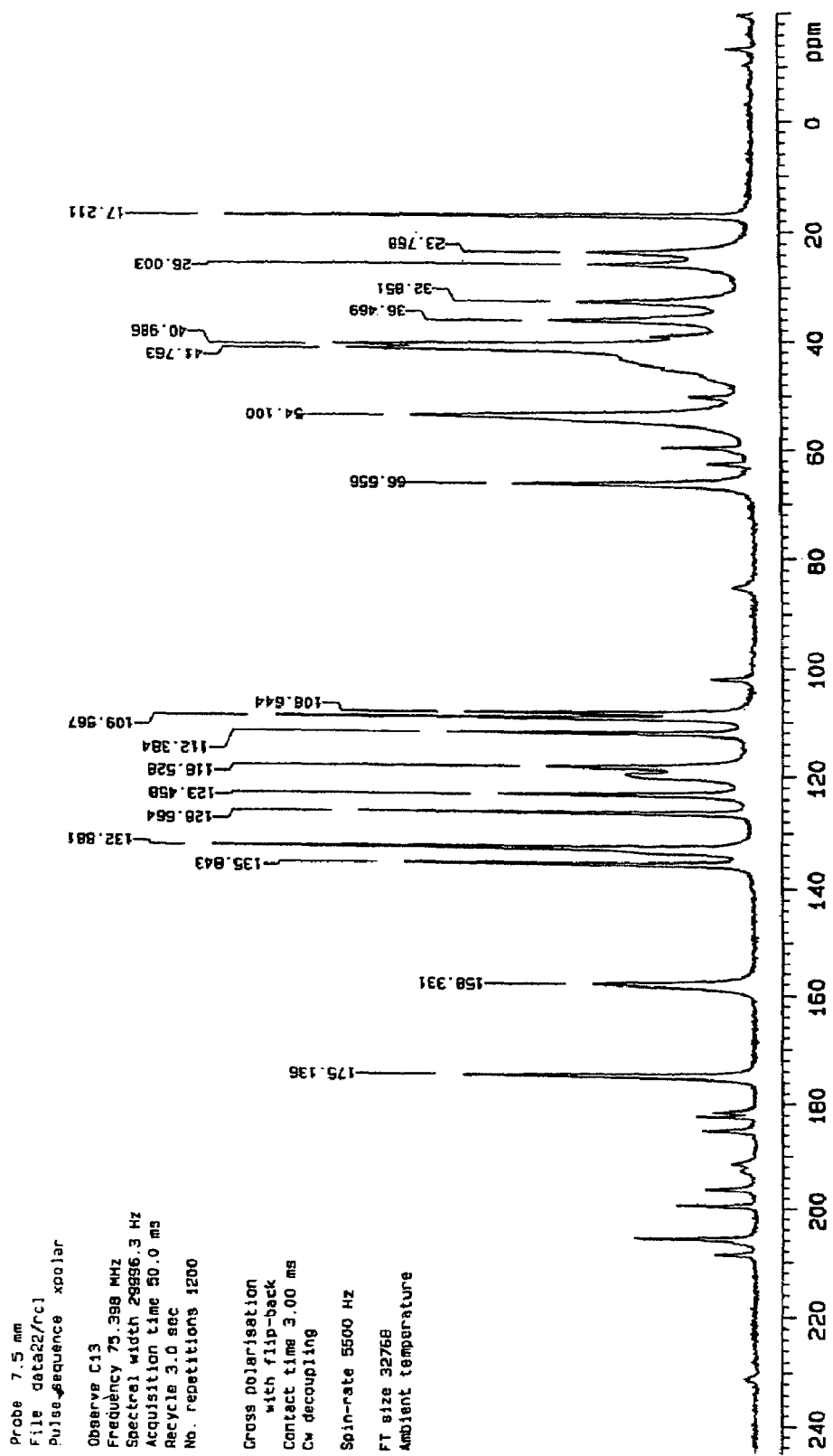
FIG. 7 is a $^{13}C$ CPMAS spectrum of cabergoline Form I obtained using 1-chloro-4-fluorobenzene as solvent (Example 4).
Figure 8:
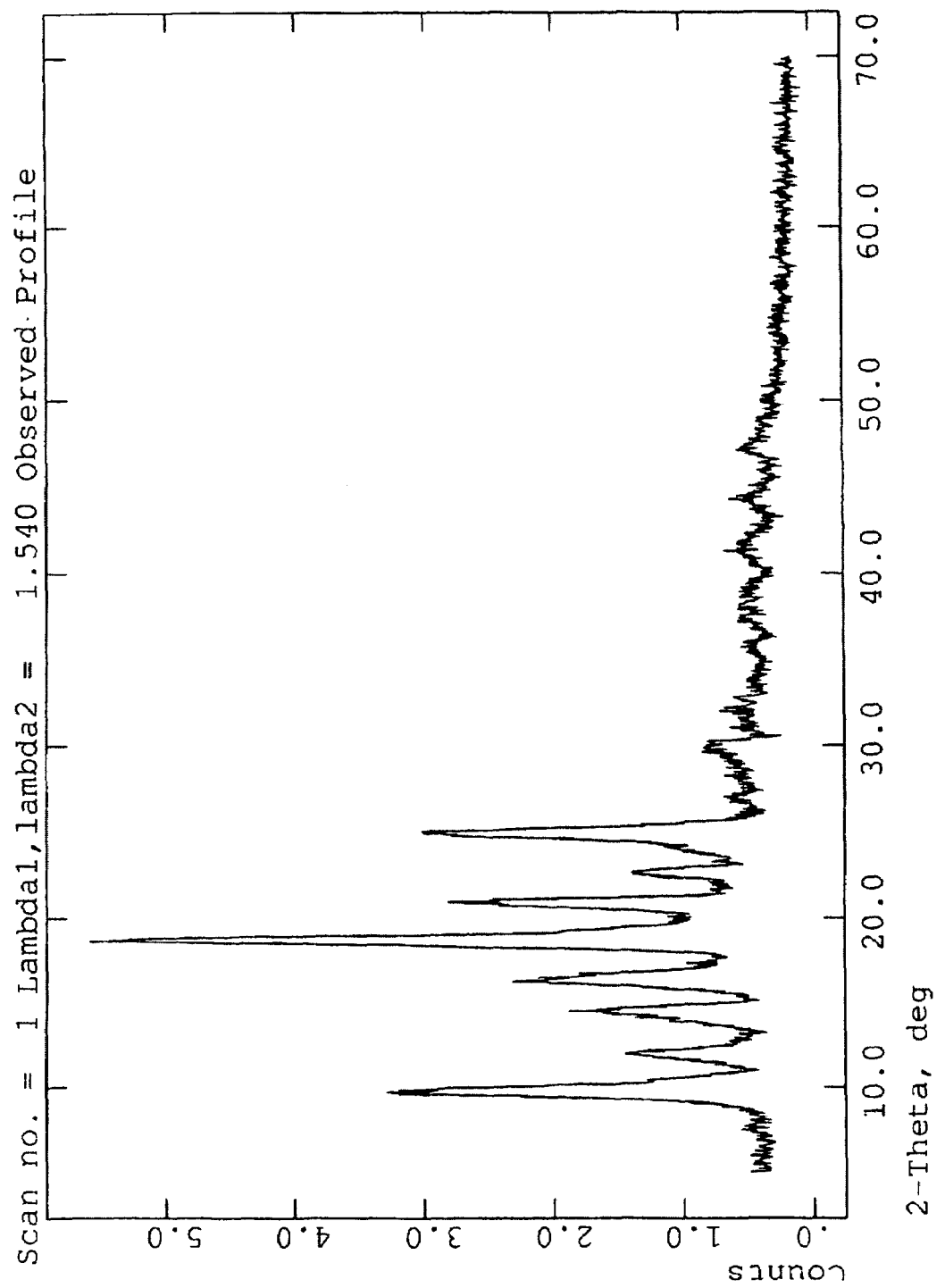
FIG. 8 is an X-ray powder diffraction pattern of cabergoline Form I obtained using 1,4-difluorobenzene as solvent (Example 6).
Figure 9:
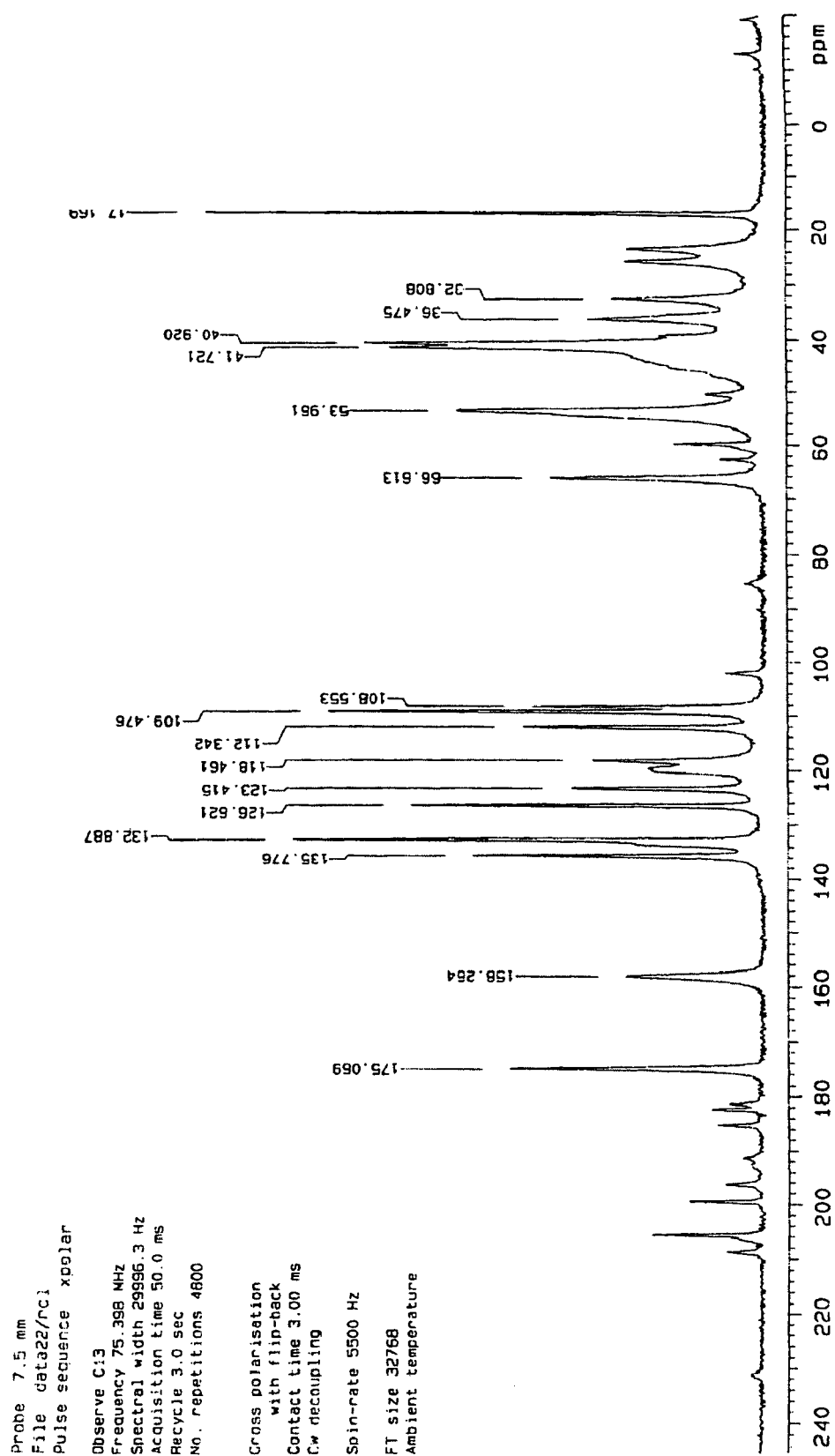
FIG. 9 is a $^{13}C$ CPMAS spectrum of cabergoline Form I obtained using 1,4-difluorobenzene as solvent (Example 6).

The present invention involves preparing cabergoline Form I by dissolving cabergoline in a p-disubstituted benzene of formula (A),

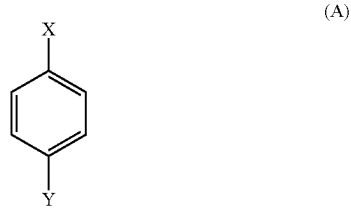

(A)

where X is a halogen, and Y is selected from the group consisting of halogens or lower alkyls to form a solution, and then recovering the cabergoline Form I polymorph. Cabergoline Form I can be recovered from the solution, suitably by direct crystallization to obtain cabergoline Form I or by recovery of a solvate which can be converted into cabergoline Form I.

Preferably, the p-disubstituted benzene of formula (A) is substituted with fluorine at the X position. More preferably, the p-disubstitued benzene of formula (A) is substituted with fluorine at the X position and where Y is selected from the group consisting of methyl, fluorine or chlorine. Most preferably, the p-disubstituted benzene of formula (A) is selected from the group consisting of 4-fluorotoluene, 1-chloro-4-fluorobenzene, or 1,4-difluorobenzene.

In one preferred embodiment of the invention, cabergoline Form I may be obtained by forming a solvate of cabergoline and a p-disubstituted benzene of formula (A), optionally further comprising an anti-solvent, and obtaining cabergoline Form I from this solvate.

In another embodiment of the present invention, cabergoline Form I is prepared by dissolving cabergoline in a solvent comprising a p-disubstituted benzene of formula (A), optionally adding an anti-solvent to form a solvate, and the solvate is dried to obtain cabergoline Form I.

In yet another embodiment of the present invention, cabergoline Form I is prepared by a method comprising dissolving cabergoline in 1,3,5-trimethylbenzene (mesitylene) and recovering the cabergoline Form I polymorph. Cabergoline Form I can be obtained from the solution in 1,3,5-trimethylbenzene, suitably by direct crystallization to obtain cabergoline Form I or by recovery of a solvate which can be converted to cabergoline Form I.

In a preferred embodiment of the present invention, cabergoline Form I is prepared by forming a solvate of cabergoline and 1,3,5-trimethylbenzene, optionally adding an anti-solvent to obtain the solvate, and obtaining cabergoline Form I from this solvate.

Another embodiment of the invention comprises dissolving cabergoline in a solvent comprising 1,3,5-trimethylbenzene, optionally adding an anti-solvent to form a solvate, and drying the solvate to obtain cabergoline Form I.

In another embodiment of the present invention, cabergoline is dissolved in a solvent which comprises a p-disubstituted benzene of formula (A) or 1,3,5-trimethylbenzene and the solution is cooled to a temperature of −5° C. or below. The solvent preferably comprises at least 75% by volume of a p-disubstituted benzene of formula (A). It is contemplated in accordance with the present invention that the solvent may consist solely of a p-disubstituted benzene of formula (A). According to another aspect of the invention, the solvent preferably comprises at least 75% by volume 1,3,5-trimethylbenzene. Furthermore, it is also contemplated, in accordance with the present invention, that the solvent may consist solely of 1,3,5-trimethylbenzene.

In a further embodiment of the present invention, cabergoline is dissolved in a solvent selected from a p-disubstituted benzene of formula (A) and 1,3,5-trimethylbenzene. The dissolving process is optionally performed at room temperature, typically about 25-30° C. and the resulting solution is preferably filtered to remove particulate material. The temperature of the solution is then lowered to about −17° C. or below, preferably −23° C. or below, thereby forming a precipitate of cabergoline. Formation of the cabergoline precipitate can optionally be encouraged by stirring or seeding using crystalline cabergoline Form I.

To the cabergoline precipitate an anti-solvent is added. As used herein, an anti-solvent is generally a liquid in which cabergoline, cabergoline/p-disubstituted benzene of formula (A) solvate and/or cabergoline/1,3,5-trimethylbenzene solvate is highly insoluble. The anti-solvent preferably comprises hexane, heptane, diethylether, diisopropylether, tertiarybutylmethyl ether or mixtures of these solvents. The anti-solvent more preferably comprises heptane, and most preferably comprises n-heptane.

The addition of the anti-solvent results in formation and precipitation of cabergoline, a cabergoline/p-disubstituted benzene of formula (A) solvate, or a cabergoline/1,3,5-trimethylbenzene solvate, forming a slurry that can be filtered to recover a solid, which is optionally washed, for example with further anti-solvent, and then dried to yield cabergoline Form I having high purity.

The ratio of the first solvent, i.e., the solvent comprising a p-disubstituted benzene of formula (A) or 1,3,5-trimethylbenzene to the second solvent, i.e., the anti-solvent, is generally in the range of 4-10:5-20 volumes, preferably in the range of 5-7:8-15 volumes and more preferably in the range of 5-7:10-12 volumes. It is most preferable that the ratio of the first solvent to the second solvent is approximately 5-6:11.

Advantageously, wet solvate of the present invention that can be recovered by filtration can be rapidly dried to form crystals of cabergoline Form I.

Drying of the wet solvate can be achieved in a number of different ways. For example, drying has been carried out under reduced pressure, at pressures of 900 mbar or less, 800 mbar or less and 700 mbar or less. In each of these examples, a dried, pure cabergoline Form I was obtained within 30 hours. Drying can also be carried out at elevated temperatures. It is contemplated in accordance with the present invention that the wet solvate can be rapidly dried at 40° C. to 60° C.

Yet another option is to dry the wet solvate in an inert gas atmosphere. The inert gas atmosphere comprises nitrogen, argon and/or other inert gases at a concentration of 80% or higher by volume. Preferably the inert gas atmosphere comprises 5% or less oxygen. In addition, a nitrogen or other inert gas blanket can be used to dry the wet solvate or drying can be carried out in a stream of an inert gas. It has been found that drying using an inert gas can be completed in less than approximately 20 hours. This is especially an advantage when preparing cabergoline Form I at large scale.

The above methods have been found, advantageously, to yield cabergoline Form I having a relatively small particle size, typically with a volume median diameter (VMD) of less than 90 microns. Example 8 below illustrates the particle size advantages associated with cabergoline Form I prepared using 4-fluorotoluene, 1-chloro-4-fluorobenzene, and 1,4-difluorobenzene respectively. Any milling of the product after crystallization tends to result in loss of polymorph purity, and therefore this relatively small particle size is a significant advantage in preparation of a pharmaceutical product having cabergoline Form I of high purity.

Also provided by the present invention is cabergoline Form I, obtained by the methods of the invention, a solvate of cabergoline comprising cabergoline and a p-disubstituted benzene of formula (A), and a solvate of cabergoline comprising cabergoline and 1,3,5-trimethylbenzene.

Figure 10:
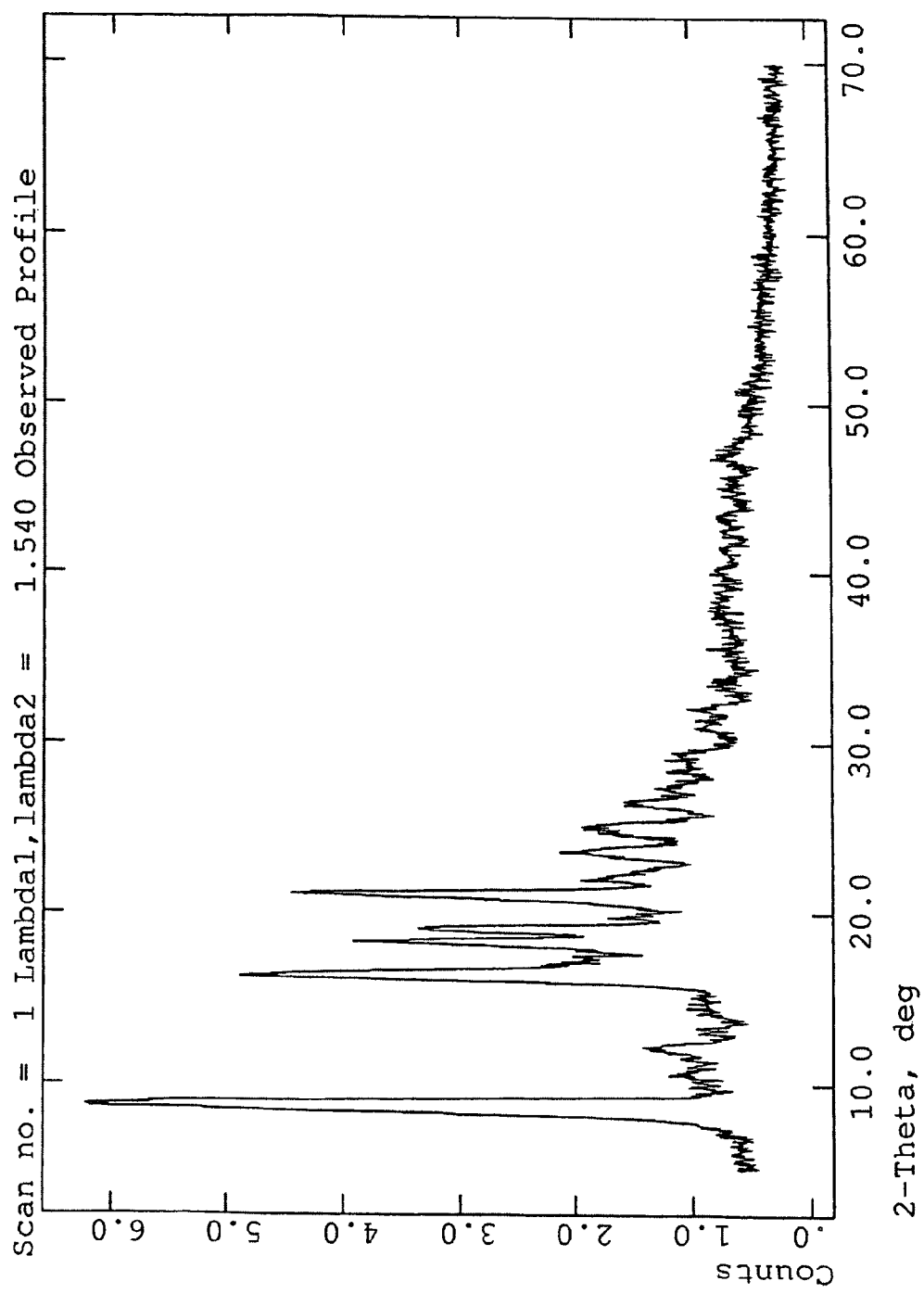
FIG. 10 is an X-ray powder diffraction pattern of cabergoline Form $F_B$.
Figure 11:
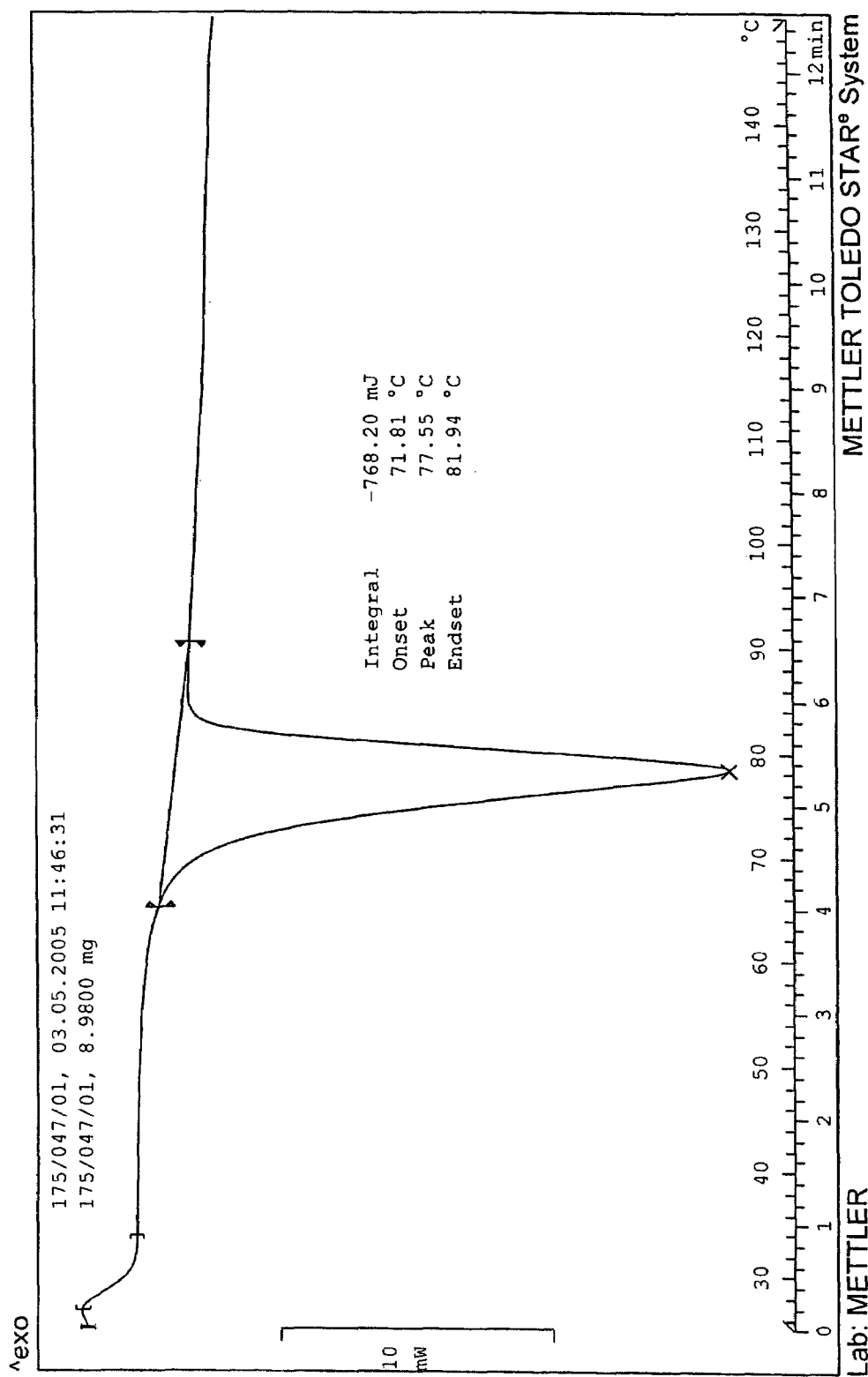
FIG. 11 is a differential scanning calorimetry (DSC) trace of damp cabergoline Form $F_B$ cabergoline obtained using fluorobenzene as solvate (Example 9)
Figure 12:
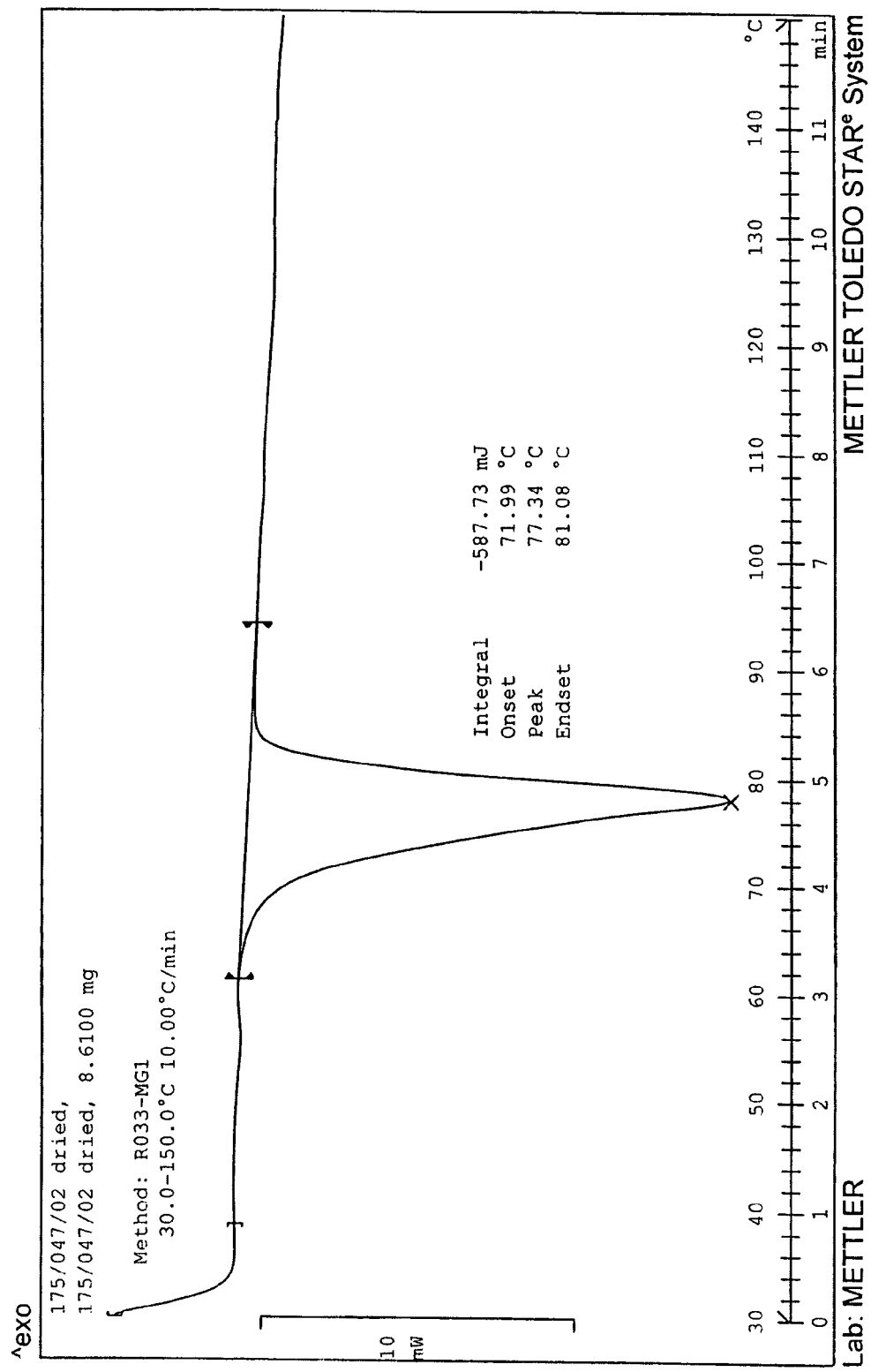
FIG. 12 shows a differential scanning calorimetry (DSC) trace of dry cabergoline Form $F_B$ obtained using fluorobenzene as solvent (Example 9). Insofar as the damp and dry DSC traces are essentially identical, it can be inferred that Form $F_B$ cabergoline is solvated.
Figure 13:
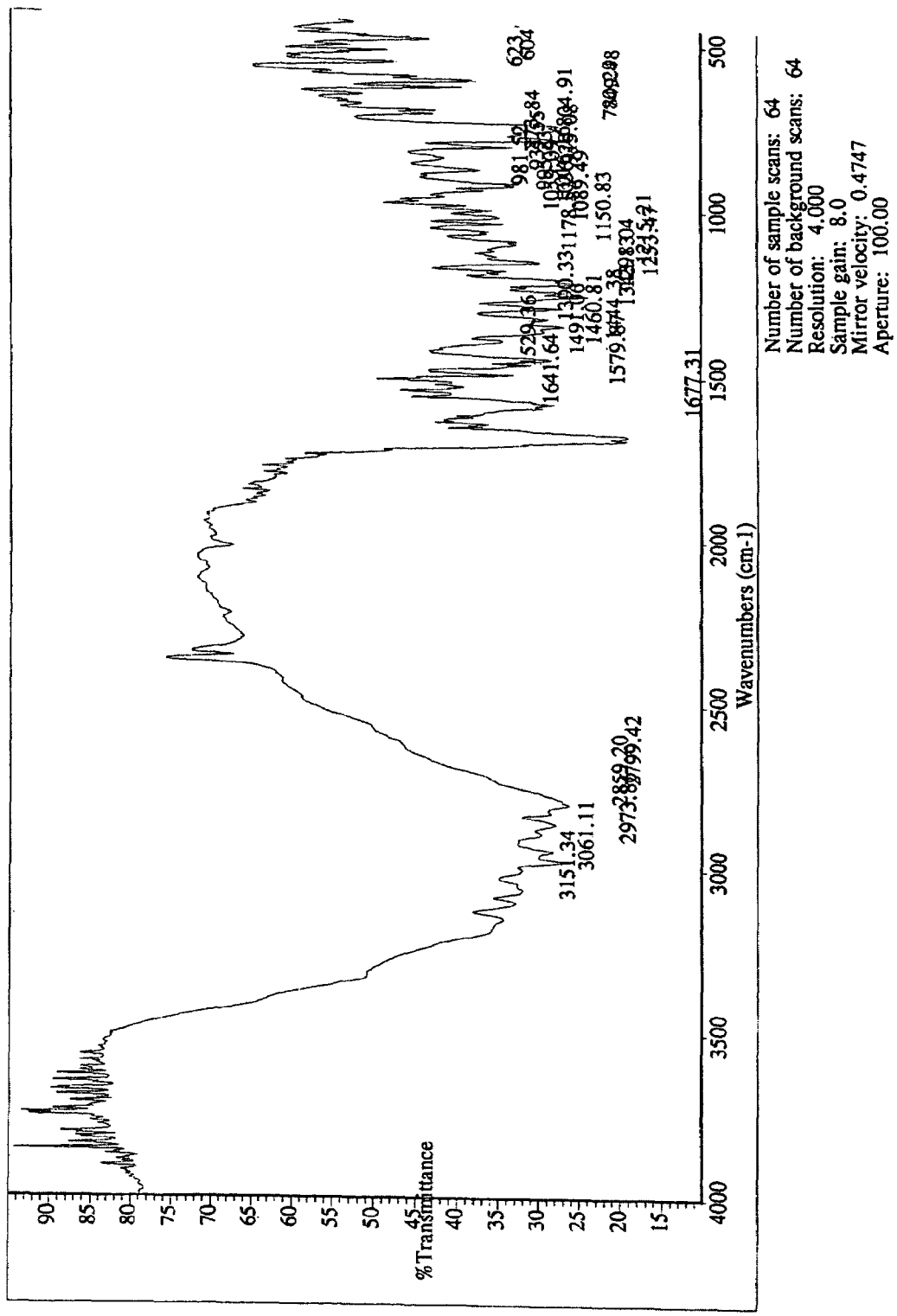
FIG. 13 is an FTIR scan of cabergoline Form $F_B$.
Figure 14:
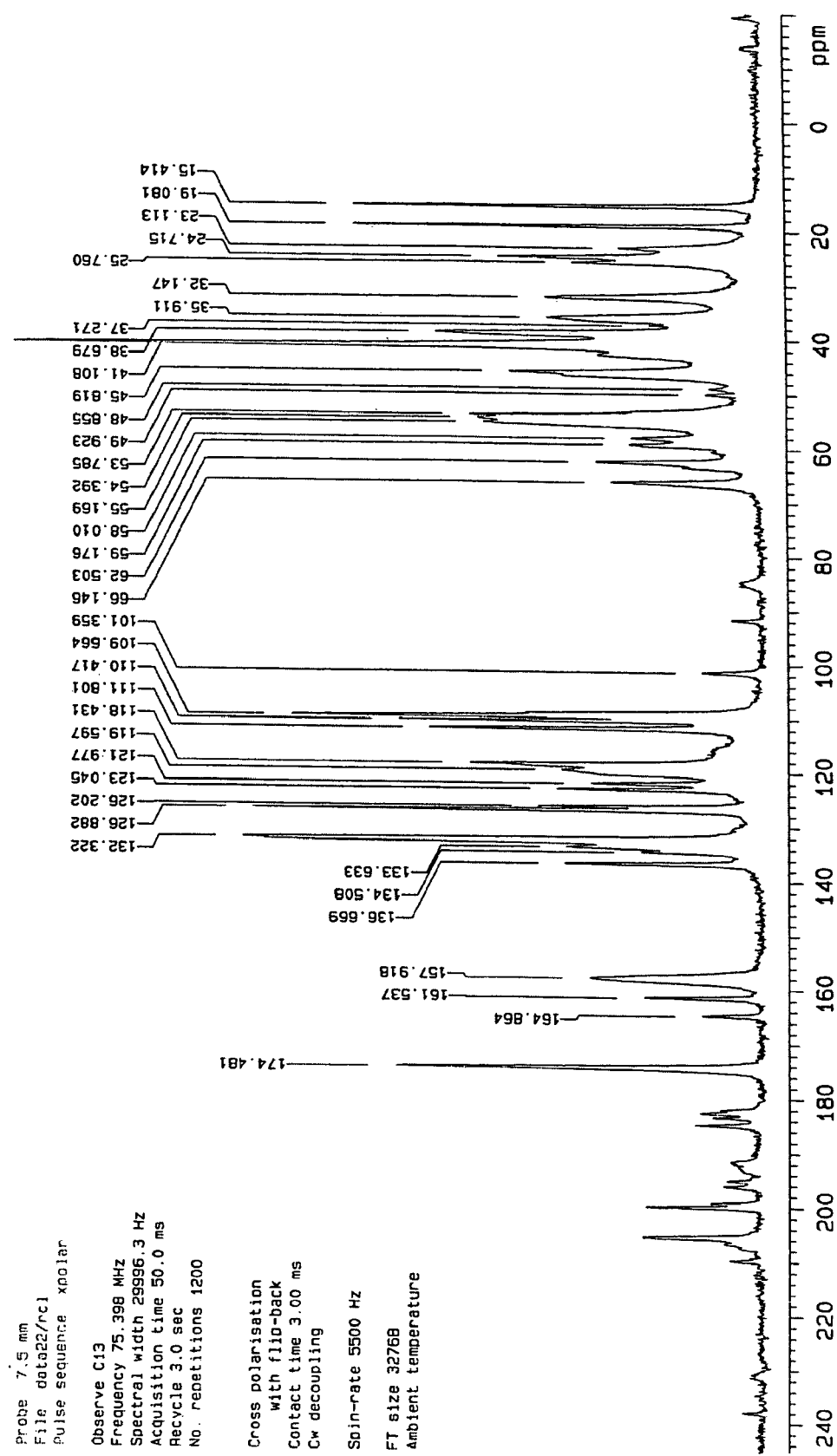
FIG. 14 is a $^{13}C$ CPMAS spectrum of cabergoline Form $F_B$.

Another aspect of this invention provides a new polymorphic form of cabergoline (designated cabergoline Form $F_B$). The new cabergoline Form $F_B$ may be characterized by the X-ray powder diffraction pattern in FIG. 10, the DSC scans in FIGS. 11 and 12, the FTIR scan in FIG. 13, or the $^{13}C$ CPMAS spectrum in FIG. 14.

Cabergoline Form $F_B$ may be prepared by a process comprising dissolving cabergoline in fluorobenzene (a p-disubstituted benzene of formula (A) where X is fluorine and Y is hydrogen), to form a solution and recovering said cabergoline Form $F_B$ from the solution.

In another embodiment, cabergoline Form $F_B$ may be prepared by a process comprising forming a solvate of cabergoline and fluorobenzene (a p-disubstituted benzene of formula (A) where X is fluorine and Y is hydrogen), and obtaining cabergoline Form $F_B$ from the solvate.

The following examples illustrate the invention without intending to limit the scope of the invention.

EXAMPLES

Example 1

Preparation of Cabergoline Form I using 4-fluorotoluene 5.0 grams of cabergoline (purity 99.9% by HPLC percentage peak area) was dissolved in 15 mL of a solvent (4-fluorotoluene) to form a solution. The solution was cooled to −20° C. to give a gel. After 7 hours, 110 mL of a pre-filtered solution of an anti-solvent (n-heptane), also at −20° C., was added dropwise over a 20-minute period.

Once the addition was complete, the slurry was stirred at −20 to −15° C. for 3.5 hours. The product was then collected by filtration under a blanket of nitrogen and the filter cake washed with cold (−20 to −15° C.) n-heptane. The filter cake was then dried under a blanket of nitrogen for 30 minutes.

The resulting solid was then placed in a vacuum oven with a nitrogen purge at 45-50° C. Full vacuum was then applied to the solid in the vacuum oven at 40 to 50° C. until the sample was at constant weight.

Samples of the product were subjected to chromatographic tests such as FTIR, DSC and X-ray crystallographic analysis (as set forth in FIG. 1) and determined to be pure cabergoline Form I. The yield was 96.7%.

Example 2

Preparation of Cabergoline Form I using 4-fluorotoluene

The procedure of Example 1 was repeated; except that 2.0 grams of cabergoline were dissolved in 10 mL of 4-fluorotoluene and 22 mL of n-heptane were added in the subsequent stage.

Samples of the product were subjected to FTIR and determined to be pure cabergoline Form I. DSC analysis of damp material showed a peak at 52.5° C. and DSC analysis of dry material showed a peak at 104.20° C. The yield was 77.8%.

Example 3

Preparation of Cabergoline Form I using 4-fluorotoluene

The procedure of Example 1 was repeated; except that 2.0 grams of cabergoline were dissolved in 6 mL of 4-fluorotoluene and 44 mL of n-heptane were added in the subsequent stage.

Samples of the product were subjected to FTIR, DSC and X-ray crystallographic analysis and determined to be pure cabergoline Form I. DSC analysis of damp material showed a peak at 52.5° C. and DSC analysis of dry material showed a peak at 104.16° C. The yield was 82%.

Example 4

Preparation of Cabergoline Form I using 1-chloro-4-fluorobenzene 2.0 grams of cabergoline was dissolved in 8 mL of solvent (1-chloro-4-fluorobenzene) by warming to form a solution. The solution was then filtered through a 0.45 µ filter which was then washed with 2 mL of 1-chloro-4-fluorobenzene. The solution was then stirred in a freezer at −15 to −20° C. for 20 hours. 44 mL of cold n-heptane was added in over 20 minutes.

Once the addition was complete, the suspension was stirred at −15 to −20° C. for 3.5 hours. The product was then collected by filtration and the filtrate was washed with cold heptane. The filtrate was then dried under a blanket of nitrogen for 30 minutes, yielding 2.3 g (damp weight) of product (DSC=67° C.).

The resulting solid was then subjected to a nitrogen flow at 40° C. followed by drying in vacuo at 40° C. for 24 hours (DSC=67° C.) and then drying the dried solid in vacuo at 50° C. for an additional 96 hours (DSC=103.1° C.).

Samples of the product at both drying stages were subjected to chromatographic tests such as FTIR, DSC and $^{13}C$ CPMAS analysis (as set forth in FIGS. 3–7) and determined to be pure cabergoline Form I.

Example 5

Preparation of Cabergoline Form I using 1-chloro-4-fluorobenzene 2.25 grams of cabergoline was dissolved in 6.75 mL of solvent (1-chloro-4-fluorobenzene) at 19.5° C. to form yellow homogenous solution. The solution was then polish filtered and the filter was washed with 2.25 mL of 1-chloro-4-fluorobenzene. The solution was then stirred in a freezer at −15 to −17° C. until a white solid precipitated without seeding. 49.5 mL of cold n-heptane was added (at −20 to −25° C.) under a blanked of nitrogen over a period of 15 minutes. The flask containing the mixture was returned to the freezer and stirred overnight.

The solid was then filtered off the next day and washed with cold filtrate (mother liquor) to help transfer the solid. The filtered solid was then kept under suction and a positive stream of nitrogen for 20 minutes and then transferred to a hot (40° C.) oven with nitrogen for 3 hours. The damp weight was 2.69 g.

The solid was then dried in an oven in vacuo at 45° C. overnight to yield 2.113 g of dry solid.

Samples of the product were subjected to DSC analysis resulting in the following results and confirming that the product formed was pure cabergoline Form I.

|  | Very Small Peak | Main Peak |
|---|---|---|
| integral | −3.23 mJ | −126.69 mJ |
| onset | 62.62° C. | 95.45° C. |
| Peak | 65.50° C. | 102.20° C. |
| endset | 68.17° C. | 104.84° C. |

Example 6

Preparation of Cabergoline Form I using 1,4-difluorobenzene 2.0 grams of cabergoline was dissolved in 6 mL of solvent (1,4-difluorobenzene) at 18° C. The solution was then polish filtered and the filter was washed with 1 mL of 1,4-difluorobenzene. The solution was then kept in a freezer at −17° C. with no stirring. No precipitate formed and the solution was seeded with cabergoline Form I and left overnight at −17° C. in a freezer with no stirring. 44 mL of cold n-heptane was added in over a period of 15 minutes. The flask containing the mixture was returned to the freezer to stand overnight −17° C. with no stirring.

The next day the solid was filtered and washed with cold filtrate (mother liquor) to help transfer the solid. The filtered solid was then kept under suction and a positive stream of nitrogen for 20 minutes and then transferred to a hot (40° C.) oven with nitrogen for 3 hours. The damp weight was 2.203 g. The solid was then dried in an oven in vacuo at 45° C. for 24 hours to yield 1.82 g of dry solid.

Samples of the product were subjected to FTIR analysis resulting in a determination that the product formed was pure cabergoline Form I.

Example 7

Preparation of Cabergoline Form I using 1,3,5-trimethylbenzene

The procedure of Example 1 was repeated using 1,3,5-trimethylbenzene (mesitylene) as the solvent. Specifically, 2.0 grams of cabergoline was dissolved in 50 mL of 1,3,5-trimethylbenzene and the resulting solution was processed as described in Example 1.

Analysis of the resulting product showed that it consisted predominantly of cabergoline Form I, together with a minor amount (3.8%) of the Form II.

Example 8

Comparison of Polymorphs Obtained from Different Solvents.

The procedure of Example 4 was repeated using the solvents indicated in the following table. The polymorphic form obtained is indicated in the right hand column.

| Solvent | Polymorphic form |
|---|---|
| 1-chloro-4-fluorobenzene/heptane | Form I |
| 4-methylanisole | Form II |
| chlorobenzene/heptane | A mixture of polymorphic forms. |
| fluorobenzene/heptane | A new polymorphic form according to DSC, X-ray and SS$^{13}$C analysis (designated Form $F_B$) |

Comparison of Particle Size of Cabergoline Polymorphs Obtained from Different Solvents.

The procedure of Example 1 was repeated using 4-fluorotoluene/heptane, 1,3,5-trimethylbenzene, 1-chloro-4-fluorobenzene/heptane, and 1,4-difluorobenzene respectively. The particle size of the cabergoline Form I polymorph obtained in each instance was measured and compared to the particle size of cabergoline Form I obtained according to WO 03/078433, disclosing the preparation from toluene/heptane and to the particle size of cabergoline Form II. The results are shown in the Table below.

| Polymorph; Solvent | $X_{10}$ μm | $X_{50}$ μm | $X_{90}$ μm | VMD μm |
|---|---|---|---|---|
| Form I 4-fluorotoluene/heptane | 1.76 | 106.21 | 158.01 | 84.95 |
| Form I 1,3,5-trimethylbenzene | 2.96 | 45.01 | 141.84 | 61.80 |
| Form I 1,chloro-4-fluorobenzene | 9.17 | 28.42 | 69.74 | 34.02 |
| Form I 1,4-difluorobenzene | 24.35 | 42.83 | 77.64 | 47.54 |
| Form I Toluene/heptane | 36.67 | 100.05 | 149.69 | 96.01 |
| Form II | 46.68 | 117.56 | 159.36 | 111.26 |

Example 9

Preparation of Cabergoline Form $F_B$ using 4-fluorobenzene 2.0 grams of cabergoline was dissolved in 4 mL of solvent (4-fluorobenzene). The solution was then filtered through a 0.45 μ filter and placed in a freezer at −15° C.

The solid formed was washed with 4 mL of n-heptane and dried under a nitrogen blanket. The solid was then placed in an oven overnight at 40° C. The following day, the solid was dried in vacuo for 30 minutes.

Samples of the product were subjected to chromatographic tests such as DRIFT IR and X-ray chromatography and found to be neither cabergoline Form I or Form II. The product is considered to be a new polymorphic form, cabergoline Form $F_B$. DSC testing of the damp and dry product (see FIGS. 11 and 12) indicate that cabergoline Form $F_B$ is solvated. This result was confirmed by gas chromatography (residual fluorobenzene solvent−9.3 wt %).

Accordingly, the present invention provides methods for obtaining crystalline cabergoline Form I with high purity, which is easy to dry from the intermediate solvate and which has a particle size that facilitates preparation of a pharmaceutical product with reduced post-crystallization processing. It also provides a new polymorphic form that is designated here as cabergoline Form $F_B$.

The use of the terms "a" and "an" and "the" and similar references in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A method of preparing cabergoline Form I, comprising: forming a solvate of cabergoline and a p-disubstituted benzene of formula (A)

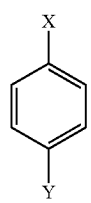

(A)

wherein X is a halogen, and Y is selected from the group consisting of halogens or lower alkyls; and, obtaining cabergoline Form I from that solvate.

2. The method of claim 1, comprising forming a solvate of cabergoline and a p-disubstituted benzene of formula (A) wherein X is fluorine.

3. The method of claim 2, comprising forming a solvate of cabergoline and a p-disubstituted benzene of formula (A) wherein Y is selected from the group consisting of a fluorine, chlorine or methyl.

4. The method of claim 3, comprising forming a solvate of cabergoline and a p-disubstituted benzene of formula (A) wherein X is fluorine and Y is chlorine.

5. The method of claim 3, comprising forming a solvate of cabergoline and a p-disubstituted benzene of formula (A) wherein X is fluorine and Y is methyl.

6. The method of claim 3, comprising forming a solvate of cabergoline and a p-disubstituted benzene of formula (A) wherein X is fluorine and Y is fluorine.

7. The method of claim 1, wherein the p-disubstituted benzene of formula (A) is 4-fluorotoluene.

8. The method of claim 1, wherein the p-disubstituted benzene of formula (A) is 1-chloro-4-fluorobenzene.

9. The method of claim 1, wherein the p-disubstituted benzene of formula (A) is 1,4-difluorobenzene.

10. The method of claim 1, where the solvate is formed by dissolving cabergoline in a solvent comprising a p-disubstituted benzene of formula (A).

11. The method of claim 10, wherein the solvent comprises at least 75% by volume of a p-disubstituted benzene of formula (A).

12. The method of claim 11, wherein the solvent comprises a p-disubstituted benzene of formula (A) alone.

13. The method of claim 10, further comprising the step of cooling the solution formed by dissolving cabergoline in a p-disubstituted benzene of formula (A) to a temperature of at most about −5° C.

14. The method of claim 10, further comprising the step of filtering the solution formed by dissolving cabergoline in a p-disubstituted benzene of formula (A).

15. The method of claim 10, further comprising the step of adding an anti-solvent to form the solvate.

16. The method of claim 15, wherein the anti-solvent is selected from the group consisting of hexane, heptane, diethylether, diisopropylether, tertiarybutylmethyl ether, and mixtures thereof.

17. The method of claim 16, wherein the anti-solvent is heptane.

18. The method of claim 17, wherein the anti-solvent is n-heptane.

19. The method of claim 1, wherein cabergoline Form I is obtained from the solvate by drying.

20. The method of claim 19, wherein the drying is performed at a pressure of 900 mbar or less.

21. The method of claim 19, wherein the drying occurs at a temperature of at least about 40° C.

22. The method of claim 19, wherein the drying occurs in an inert gas atmosphere.

23. The method of claim 22, wherein the inert gas atmosphere comprises less than 5% of oxygen.

24. The method of claim 22, wherein the inert gas atmosphere comprises an inert gas selected from the group consisting of nitrogen gas and argon gas.

25. The method of claim 22, wherein the inert gas atmosphere comprises a gas mixture including at least about 80% inert gas.

26. The method of claim 25, wherein the gas mixture comprises nitrogen gas.

27. The method of claim 25, wherein the gas mixture comprises argon gas.

28. A solvate of cabergoline comprising cabergoline and a p-disubstituted benzene of formula (A)

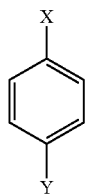

(A)

wherein X is a halogen, and Y is selected from the group consisting of halogens or lower alkyls.

29. The solvate of claim 28, comprising cabergoline and a p-disubstituted benzene of formula (A) wherein X is fluorine.

30. The solvate of claim 29, comprising cabergoline and a p-disubstituted benzene of formula (A) wherein Y is selected from the group consisting of a fluorine, chlorine or methyl.

31. The solvate of claim 30, comprising cabergoline and a p-disubstituted benzene of formula (A) wherein X is fluorine and Y is chlorine.

32. The solvate of claim 30, comprising cabergoline and a p-disubstituted benzene of formula (A) wherein X is fluorine and Y is methyl.

33. The solvate of claim 30, comprising cabergoline and a p-disubstituted benzene of formula (A) wherein X is fluorine and Y is fluorine.

34. The solvate of claim 28, wherein the p-disubstituted benzene of formula (A) is 4-fluorotoluene.

35. The solvate of claim 28, wherein the p-disubstituted benzene of formula (A) is 1-chloro-4-fluorobenzene.

36. The solvate of claim 28, wherein the p-disubstituted benzene of formula (A) is 1,4-difluorobenzene.

37. The solvate of claim 31, further comprising an anti-solvent.

38. The solvate of claim 37, wherein the anti-solvent is selected from the group consisting of hexane, heptane, diethylether, diisopropylether, tertiarybutylmethyl ether, and mixtures thereof.

39. The solvate of claim 38, wherein the anti-solvent is heptane.

40. The solvate of claim 39, wherein the anti-solvent is n-heptane.

41. A method of preparing cabergoline Form I comprising dissolving cabergoline in a solvent comprising a p-disubstituted benzene of formula (A)

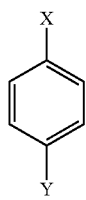

(A)

wherein X is a halogen, and Y is selected from the group consisting of a halogen or a lower alkyl to form a solution and obtaining cabergoline Form I from the solution.

42. The method of claim 41, wherein the solvent comprises a p-disubstituted benzene of formula (A) wherein X is fluorine.

43. The method of claim 42, wherein the solvent comprises a p-disubstituted benzene of formula (A) wherein Y is selected from the group consisting of a fluorine, chlorine or methyl.

44. The method of claim 43, wherein the solvent comprises a p-disubstituted benzene of formula (A) wherein X is fluorine and Y is chlorine.

45. The method of claim 43, wherein the solvent comprises a p-disubstituted benzene of formula (A) wherein X is fluorine and Y is methyl.

46. The method of claim 43, wherein the solvent comprises a p-disubstituted benzene of formula (A) wherein X is fluorine and Y is fluorine.

47. The method of claim 41, wherein the p-disubstituted benzene of formula (A) is 4-fluorotoluene.

48. The method of claim 41, wherein the p-disubstituted benzene of formula (A) is 1-chloro-4-fluorobenzene.

49. The method of claim 41, wherein the p-disubstituted benzene of formula (A) is 1,4-difluorobenzene.

50. The method of claim 41, wherein the solvent comprises at least 75% by volume of said p-disubstituted benzene of formula (A).

51. The method of claim 50, wherein the solvent comprises a p-disubstituted benzene of formula (A) alone.

52. The method of claim 41, further comprising the step of cooling the solution to a temperature of at most about −5° C.

53. The method of claim 41, wherein the dissolving takes place at room temperature.

54. The method of claim 53, wherein the dissolving takes place between 25-30° C.

55. The method of claim 41, further comprising the step of filtering the solution to remove particulate material.

56. The method of claim 41, further comprising the step of cooling the solution to a temperature of at most about −17° C. to form a precipitate.

57. The method of claim 56, wherein the solution is cooled to a temperature of at most about −23° C. to form a precipitate.

58. The method of claim 41, further comprising the step of adding a second solvent to the solution.

59. The method of claim 58, wherein the second solvent is selected from the group consisting of hexane, heptane, diethylether, diisopropylether, tertiarybutylmethyl ether, and mixtures thereof, wherin the second solvent is an anti-solvent.

60. The method of claim 59, wherein the anti-solvent is heptane.

61. The method of claim 60, wherein the anti-solvent is n-heptane.

62. The method of claim 59, where the ratio of the p-substituted benzene of formula (A) to the second solvent is 4-10:5-20 volumes.

63. The method of claim 62, where the ratio of the p-substituted benzene of formula (A) to the second solvent is 5-7:10-12 volumes.

64. The method of claim 63, where the ratio of the p-substituted benzene of formula (A) to the second solvent is 5-6:11 volumes.

65. The method of claim 41, further comprising the step of drying the solution to obtain cabergoline Form I.

66. The method of claim 65, wherein the drying is performed at a pressure of 900 mbar or less.

67. The method of claim 65, wherein the drying occurs at a temperature of at least about 40° C.

68. The method of claim 65, wherein the drying occurs in an inert gas atmosphere.

69. The method of claim 68, wherein the inert gas atmosphere contains less than 5% oxygen.

70. The method of claim 68, wherein the inert gas atmosphere comprises an inert gas selected from the group consisting of nitrogen gas and argon gas.

71. The method of claim 68, wherein the inert gas atmosphere comprises a gas mixture including at least about 80% inert gas.

72. The method of claim 71, wherein the gas mixture comprises nitrogen gas.

73. The method of claim 71, wherein the gas mixture comprises argon gas.

74. A method of preparing cabergoline Form I, comprising forming a solvate including cabergoline and 1,3,5-trimethylbenzene by dissolving cabergoline 1,3,5-trimethylbenzene to form a solution and obtaining cabergoline Form I from the solvate by filtering said solution.

75. The method of claim 74, wherein the cabergoline Form I is obtained from the solvate by drying at a pressure of 900 mbar or less, at a temperature of at least 40° C. and in an inert gas atmosphere that contains less than 5% of oxygen.

76. A solvate of cabergoline comprising cabergoline and 1,3,5-trimethylbenzene and an anti-solvent.

77. The solvate of claim 76, wherein the anti-solvent is selected from the group consisting of hexane, heptane, diethylether, diisopropylether, tertiarybutylmethyl ether, and mixtures thereof.

78. The solvate of claim 77, wherein the anti-solvent is heptane.

79. A method of preparing cabergoline Form I comprising dissolving cabergoline in a solvent including 1,3,5-trimethylbenzene to form a solution and obtaining cabergoline Form I from the solution, wherein said dissolving takes place at room temperature.

80. The method of claim 79, wherein the dissolving takes place between 25-30° C.

81. The method of claim 80, further comprising the step of filtering the solution to remove particulate material.

82. The method of claim 80, further comprising the step of cooling the solution to a temperature of at most about −17° C. to form a precipitate.

83. The method of claim 82, wherein the solution is cooled to a temperature of at most about −23° C. to form a precipitate.

84. The method of claim 79, further comprising the step of adding a second solvent to the solution, wherein the second solvent is selected from the group consisting of hexane, heptane, diethylether, diisopropylether, tertiarybutylmethyl ether, and mixtures thereof, wherein the second solvent is an anti-solvent, and wherein the ratio of 1,3,5-trimethylbenzene to the second solvent is 4-10:5-20 volumes.

85. The method of claim 84, where the ratio of 1,3,5-trimethylbenzene to the second solvent is 5-7:10-12 volumes.

86. The method of claim 85, where the ratio of 1,3,5-trimethylbenzene to the second solvent is 5-6:11 volumes.

87. The method of claim 79, further comprising the step of drying the solution to obtain cabergoline Form I at a pressure of 900 mbar or less, at a temperature of at least 40° C. and in an inert gas atmosphere that contains less than 5% of oxygen.

88. Cabergoline Form $F_B$, wherein the cabergoline Form $F_B$ has an X-ray powder diffraction pattern, a differential scanning calorimetry (DSC) trace, Fourier Transform Infrared (FTIR) scan and $^{13}C$ Cross Polarization Magic Angle Spinning Nuclear Magnetic Resonance (CPMAS NMR) spectrum, as shown in FIGS. 10-14.

89. A method of preparing cabergoline Form $F_B$, comprising dissolving cabergoline in a solvent of fluorobenzene to form a solution and obtaining cabergoline Form $F_B$ from that solution.

90. The method of claim 89, further comprising the step of filtering the solution of cabergoline in fluorobenzene.

91. The method of claim 89, further comprising the step of drying the solution to obtain cabergoline Form $F_B$.

92. The method of claim 91, wherein the drying occurs in an inert gas atmosphere.

93. The method of claim 89, further comprising the step of adding a second solvent to the solution.

94. The method of claim 93, wherein the second solvent is n-heptane.

95. A method of preparing cabergoline Form $F_B$, comprising forming a solvate of cabergoline and fluorobenzene and obtaining cabergoline $F_B$ from the solvate.

* * * * *